US006843890B1

United States Patent
Godbole

(10) Patent No.: US 6,843,890 B1
(45) Date of Patent: *Jan. 18, 2005

(54) PURIFICATION AND RECOVERY OF ACETONITRILE FROM WASTE SOLVENT ACETONITRILE

(75) Inventor: Sanjay Purushottam Godbole, Solon, OH (US)

(73) Assignee: The Standard Oil Company, Warrenville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/360,327

(22) Filed: Jul. 23, 1999

(51) Int. Cl.[7] .......................... B01D 3/38; C07C 255/00
(52) U.S. Cl. ............................ 203/78; 203/79; 203/80; 203/92; 203/93; 203/94; 203/96; 203/97; 203/98; 558/441
(58) Field of Search ..................... 203/99, DIG. 19, 203/91–98, 73–80; 558/320, 466, 441

(56) References Cited

U.S. PATENT DOCUMENTS

| | | | | |
|---|---|---|---|---|
| 3,399,120 A | * | 8/1968 | Lovett | 203/84 |
| 3,445,347 A | * | 5/1969 | Borrel et al. | 203/96 |
| 3,896,007 A | * | 7/1975 | Roscalli et al. | 203/85 |
| 4,119,497 A | * | 10/1978 | Ocampo et al. | 203/29 |
| 4,269,667 A | * | 5/1981 | Landis | 203/76 |
| 4,308,108 A | * | 12/1981 | Higuchi et al. | 203/91 |
| 4,362,603 A | * | 12/1982 | Presson et al. | 203/80 |
| 4,377,444 A | * | 3/1983 | Wu | 203/96 |
| 4,404,064 A | * | 9/1983 | Lovett | 203/DIG. 19 |

* cited by examiner

Primary Examiner—Virginia Manoharan
(74) Attorney, Agent, or Firm—Thomas E. Nemo

(57) ABSTRACT

A process of treating waste solvent acetonitrile streams which contain at least one water extractable impurity such as isopropyl acetate to remove substantially all of the impurity by distilling the waste solvent acetonitrile in the presence of water for a time sufficient to allow the water extractable impurity to be extractively distilled from the acetonitrile. In preferred embodiments of the present invention the feed may contain either a mixture of waste solvent acetonitrile and crude acetonitrile or crude acetonitrile free of hydrogen cyanide by itself.

13 Claims, 1 Drawing Sheet

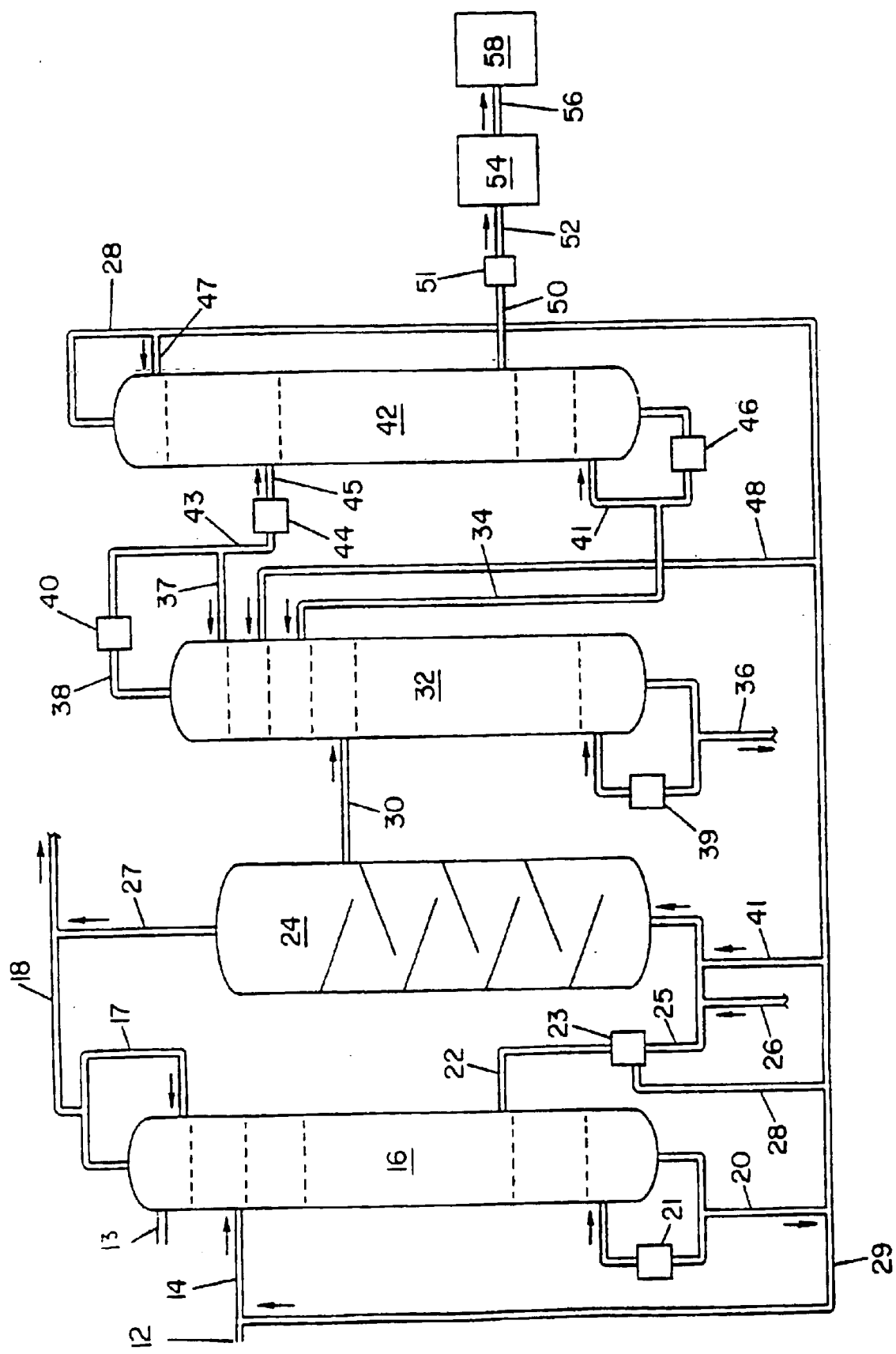

PURIFICATION AND RECOVERY OF ACETONITRILE FROM WASTE SOLVENT ACETONITRILE

BACKGROUND OF THE INVENTION

Field of the Invention

The present invention is directed to the recovery and purification of acetonitrile from waste solvent acetonitrile. For purpose of the present application the term "waste solvent acetonitrile" shall mean a mixture of acetonitrile containing impurities such as water, isopropyl acetate, isopropyl alcohol, heptane, trimethyl silanol, hexamethyl disiloxane, methanol, benzene, n-heptanes and tetrahydofuran, acrolein, oxazole, cis and trans crotonitrile, methacrylonitrile and allyl alcohol. The relative proportions of the components of the waste solvent acetonitrile can vary over a wide range depending on various conditions. The concentration level of the organic impurities in the waste solvent acetonitrile is usually less than 25% with no single organic component found in greater than 2 to 10 wt % concentration. Typically, solvent waste acetonitrile contains between 25 and 85% acetonitrile and is free of acrylonitrile and hydrogen cyanide. Prior to the invention set forth in this application waste solvent acetonitrile was usually burned or otherwise safely disposed.

The present invention is directed to a process by which waste solvent acetonitrile free of acrylonitrile and hydrogen cyanide is treated to obtain purified acetonitrile which is recovered and sold.

SUMMARY OF THE INVENTION

It is a primary object of the present invention to produce and recover purified acetonitrile from waste solvent acetonitrile.

It is a another object of the present invention to provide a process for the substantial removal of impurities present in waste solvent acetonitrile or a mixture of waste solvent acetonitrile and crude acetonitrile obtained as a coproduct during the manufacture of acrylonitrile.

It is a further object of the present invention to provide a process for the treatment of crude acetonitrile which is free of hydrogen cyanide to remove substantially all other remaining impurities.

Additional objects, advantages and novel features of the invention will be set forth in part in the description which follows, and in part will become apparent to those skilled in the art upon examination of the following or may be learned by the practice of the invention. The objects and advantages of the invention may be realized and obtained by means of the instrumentalities and combinations particularly pointed out in the appended claims.

To achieve the foregoing objects in accordance with the purpose of the present invention as embodied and described therein, the method of the present invention comprises feeding waste solvent acetonitrile containing at least one water extractable impurity (e.g. isopropyl acetate) and water into the upper portion of a distillation column, distilling the waste solvent acetonitrile in the presence of the water for a time sufficient to allow substantially all of the water extractable impurity in the waste solvent acetonitrile to be extracted by the water and removed as an overhead stream from the distillation column, recovering the acetonitrile substantially free of water extractable impurity from the lower portion of the distillation column.

In a preferred embodiment of the present invention the water is fed to the distillation column above the point where the waste solvent acetonitrile enters the distillation column.

In a further preferred embodiment of the present invention the distillation column is equipped with trays and the water is fed into the distillation column at a point above the highest trays present in the distillation column.

In a still further preferred embodiment of the process of the present invention the distillation temperature is between about 140° F. to 190° F. (preferably 164° F. to 185° F., especially preferred being 170° F. to 176° F.) at a pressure of about 18 psia.

In accordance with another aspect of the present invention as embodied and described herein, the method of the present invention comprises feeding waste solvent acetonitrile containing at least one water extractable impurity (e.g. isopropyl acetate), crude acetonitrile containing at least acrylonitrile as an impurity (other impurities may include hydrogen cyanide, acetone, acrolein, oxazole, methanol, and hexamethyldisiloxane) and water into the upper portion of a distillation column affixed with a first overhead reflux loop at a first pressure of at least 1 atmosphere and distilling the waste water acetonitrile and crude acetonitrile in the presence of the water for a time sufficient to allow substantially the water extractable impurities to be extractively distilled and removed as an overhead stream from the first distillation column producing a first acetonitrile/water azeotrope substantially free of water extractable impurities as well as light impurities and a first bottom product containing water, distilling the first azeotrope in a second distillation column affixed with a second overhead reflux loop at a second pressure less than 1 atmosphere to separate the first azeotrope into a second bottoms product containing water and an overhead stream comprising a second azeotrope having a greater concentration of acetonitrile than the first azeotrope, distilling the first azeotrope in a second distillation column affixed with a second overhead reflux loop at a second pressure less than 1 atmosphere to separate the first azeotrope into a second bottoms product containing water and an overhead stream comprising a second azeotrope having a greater concentration of acetonitrile than the first azeotrope, distilling the second azeotrope in a third distillation column affixed with a third overhead reflux loop at a third pressure above 1 atmosphere to produce a third acetontrile/water azeotrope containing substantially all the water from the second azeotrope, a third bottoms product comprising acetontrile and heavy organics, and a sidestream comprising highly pure acetonitrile.

In a preferred embodiment of this aspect of the present invention the crude acetonitrile fed with waste solvent acetonitrile into the first distillation column is substantially free or completely free of hydrogen cyanide.

In a further preferred embodiment of this aspect of the present invention the crude acetonitrile free or substantially free of hydrogen cyanide is fed into the first distillation tower without any waste solvent acetonitrile.

The term "reflux ratio" as used above is defined as follows: for the first column (light ends column), the reflux ratio is defined as the ratio of overhead reflux flow rate divided by the rate of feed from the column side to the digester. For the second distillation (drying column), the reflux ratio is defined as the ratio of overhead reflux flow rate to the rate of the overhead draw-off to the product column. For the third distillation column (product column), the reflux ratio is defined as the ratio of overhead reflux flow rate to the rate of acetonitrile product side stream flow.

In a preferred embodiment of the present invention the light ends column reflux ratio is preferably greater than 4.4 to 1, the drying column reflux ratio is preferably greater than 4.5 to 1 and the product column reflux ratio is preferably greater than 8 to 1. Especially preferred is a light ends column reflux ratio of greater than 5.2 to 1, a drying column reflux ratio of greater than 5 to 1 and a product column reflux ratio of greater than 10.9 to 1.

The term "crude acetonitrile" means liquid acetonitrile containing hydrogen cyanide, water and other impurities. The other impurities may include acrylonitrile, acetaldehyde, acetone, methanol, acrolein, oxazole, cis- and trans-crotononitrile, methacrylonitrile and allyl alcohol. The relative proportions of the components of the crude acetonitrile can vary over a wide range depending on various conditions. The concentration level of the organic impurities in the crude acetonitrile is usually less than 15% with no single organic component found in greater than 2 to 4 wt % concentration. Usually crude acetonitrile obtained from an acrylonitrile plant contains between 25 and 85% acetonitrile. Typically, the crude acetonitrile is composed on a weight basis of 52% acetonitrile, 43.6% water, 2.5% hydrogen cyanide, 0.5% acrylonitrile and 1.3% other organic impurities as mentioned above.

DESCRIPTION OF THE DRAWING

The FIGURE is a flow diagram of the practice of the process of the present invention.

DETAILED DESCRIPTION OF THE INVENTION

In accordance with the present invention, waste solvent acetonitrile either alone, or in combination with crude acetonitrile is fed with water into the upper portion of a first distillation column. The acetonitrile is then distilled in the presence of the water for a time sufficient to allow substantially all the water extractable impurities present in the acetonitrile to be extractively distilled by the water and removed in an overhead stream exiting the distillation column. The acetonitrile recovered from the lower portion of the distillation column preferably as a sidestream is substantially free of not only water extractable impurities such isopropyl acetate but also other impurities such as acrylonitrile, acetone, oxazole, etc.

In another aspect of the present invention the acetonitrile obtained in the first distillation step is further processed to manufacture "highly pure" acetonitrile. By "highly pure" acetonitrile is meant High Performance Liquid Chromatograph (HPLC) grade acetonitrile, acetonitrile of extremely high purity and being sufficiently free of UV absorbing impurities (well below 0.1 to 0.3 ppm max) having a UV absorbance cut off of <190 nm.

In a further aspect of the practice of the present invention the crude acetonitrile fed to the first distillation column is free or substantially free of any hydrogen cyanide.

The waste solvent acetonitrile stream which is processed in accordance with the present invention normally contains over 75.0% acetontrile, about 9% water and isopropyl acetate, isopropyl alcohol, hexamethyldisiloxane, trimethylsilanol and benzene as the main impurities.

With reference to the FIGURE the process of the present invention will now be set forth in detail.

The waste solvent acetonitrile is fed via inlet line 14 and water via inlet line 12 or optionally via line 13 are fed into light ends column 16 wherein acetonitrile is distilled at a temperature of between about 140° F. to 190° F. (preferably 164° F. to 185° F., especially preferred being 170° F. to 176° F.) at a pressure of about 18 psia for a time sufficient to allow a substantial amount of the impurities in the waste solvent acetonitrile to be extractively distilled by the water fed into column 16 and removed via line 18. The light impurities (e.g. isopropyl acetate, oxazole) in the waste solvent acetonitrile feed either by their boiling point or due to the presence of the water feed are also withdrawn from column 16 as a vapor draw via line 18 and refluxed back into the upper region of column 16 via reflux line 17. Preferably, the reflux ratio as defined above is greater than 3:1. Unrecovered overheads are removed via line 18 and transported to vent scrubbers or condensers (not shown) for waste treatment. Water is recovered from the bottom of light ends column 16 and discharged via line 20 to waste treatment with partial recycle through reboiler 21. A first acetonitrile/water azeotrope containing about 70% acetonitrile, less than 30% water, less than 50 ppm HCN, less than 5000 ppm isopropyl acetate and very small amounts of heavy organics is recovered via line 22 as a vapor side draw condensed in condenser 23 and transported via line 25 to digester 24.

If one is processing a mixture of waste solvent acetonitrile and crude acetonitrile obtained by ammoxidation of propylene to acrylonitrile a HCN digester composition comprising an aqueous solution of sodium hydroxide and formaldehyde is added via line 26 to digester 24 so that the HCN and acrylonitrile in the first azeotrope is destroyed.

The HCN-free acetonitrile/heavy organics and water mixture passing out of digester 24 is charged via line 30 into drying column 32 and unrecovered material is removed from digester 24 as overheads via line 27 and combined in line 18 for transport to vent scrubber and/or waste treatment. In addition, a stream comprising acetonitrile containing a small amount of heavy impurities is also charged into drying column 32 via line 34 from product column 42. In drying column 32, the acetonitrile/heavy organics and water mixture is distilled at a pressure below one atmosphere, e.g. 3.4 psi and heavy organics are discharged for waste treatment via line 36 with some recycled back via reboiler 39 into the bottom of column 32, and a gaseous top draw comprising a second acetonitrile/water azeotrope, the second azeotrope containing about 10% water, is removed from column 32 via line 38. This second azeotrope is condensed through condenser 40 and part of the condensed stream is refluxed back into column 32 via reflux line 37. The reflux ratio in this step as defined above is greater than 3.4:1.

The second acetonitrile/water azeotrope is charged via line 38 into condenser 40 where it is condensed, passed via line 43 through heat exchanger 44 where it is heated, and then charged via line 45 into product column 42. In product column 42, the second acetonitrile/Water azeotrope is distilled at high pressure, e.g. 50 psia, into three streams. A bottoms product comprising acetonitrile containing heavy impurities is withdrawn from the bottom of product column 42 into reboiler 46 for partial recycling to column 42 via line 41 and drying column 32 via line 34. A third acetonitrile/water azeotrope is withdrawn from the top of product column 42 via line 28 and condensed and recycled as reflux back to the top of product column 42 via reflux line 47. The uncondensed vapors continue via line 28 to the azeotrope condenser 23 where they are mixed with the first azeotrope. Alternatively, these uncondensed vapors may be rerouted to light ends column 16 via lines 29 and 14. Preferably, the reflux ratio as defined above of greater than 6.4:1 for this step of the process. In an alternative embodiment of the present invention, some liquid from product column overhead stream 28 may be recycled to drying column 32 via line 48 or digester 24 via line 41. Because product column 42 is operated at high pressure, all of the water in the second acetonitrile/water azeotrope charged into product column 42 is recovered in the overhead stream of product column 42, i.e. the third acetonitrile/water azeotrope, leaving high purity acetonitrile in the product column. This high purity acetonitrile (99.8 wt % acetonitrile) is drawn off column 42 as a sidestream via line 50 (This stream may be a vapor or liquid, preferably a vapor), and after cooling in heat exchanger 51 is discharged via line 52 into resin treatment bed 54 where it is treated to produce HPLC grade acetonitrile which is recovered via line 56 in product tank 58.

The temperature for distillation in drying column 32 fluctuates between about 75° F. to 90° F., preferably between 78° F. to 88° F. The typical distillation temperature in the product column is between about 250° F. to 260° F., preferably 255° F. to 258° F.

The above description is not intended to be exhaustive or limiting as to the description of the present invention, but merely as illustrative of the practice of the process of the present invention. It is evident that many alternatives, modifications and variations will be apparent to those skilled in the art in light of the foregoing description. Accordingly, it is intended to embrace all such alternatives, modifications and variations as fall within the spirit and broad scope of the appended claims.

I claim:

1. A process for treatment of waste solvent acetonitrile free of acrylonitrile and hydrogen cyanide and containing at least one impurity which is extractable with water to obtain acetonitrile having substantially all of the water extractable impurities removed comprising feeding water and said waste solvent acetonitrile into the upper portion of a distillation column, distilling the waste solvent acetonitrile in the presence of the water for a time sufficient to allow substantially all of the water extractable impurity to be extractively distilled and removed as an overhead stream from the distillation column, recovering the acetonitrile substantially free of water extractable impurity from the lower portion of the distillation column.

2. The process of claim 1 wherein the water extractable impurity is isopropyl acetate.

3. The process of claim 1 wherein the water is fed to the distillation column above the point where the waste water solvent acetonitrile enters the distillation column.

4. The process of claim 3 wherein the distillation column is equipped with trays.

5. The process of claim 4 wherein the water is fed into the distillation column at a point above the highest tray in the distillation column.

6. The process of claim 1 wherein the distillation column is operated at a temperature of about 140° F. to about 190° F.

7. A process for treating waste solvent acetonitrile free of acrylonitrile and hydrogen cyanide and crude acetonitrile obtained during the production of acrylonitrile comprising feeding water, said waste solvent acetonitrile and the crude acetonitrile into the upper portion of a first distillation column affixed with a first overhead reflux loop at a first pressure of at least 1 atmosphere and distilling said waste solvent acetontrile and crude acetonitrile in the presence of the water for a time sufficient to allow substantially all of the impurities to be extractively distilled and removed as an overhead stream from the first distillation column and, producing a first acetonitrile-water azeotrope as a side draw from the first distillation column substantially free of impurities and a first bottom product containing water, distilling the first azeotrope in a second distillation column affixed with a second overhead reflux loop at a second pressure less than 1 atmosphere to separate the first azeotrope into a second bottoms product containing water and a second acetonitrile-water azeotrope having a greater concentration of acetonitrile than the first azeotrope, distilling the second azeotrope in a third distillation column affixed with a third overhead reflux loop at a third pressure above 1 atmosphere to produce a third acetonitrile-water azeotrope containing substantially all the water from the second azeotrope, a third bottoms product comprising acetonitrile and heavy organics, and a sidestream comprising purified acetonitrile.

8. The process of claim 7 wherein the first overhead reflux loop has a reflux ratio of greater than 4.4:1.

9. The process of claim 8 wherein the second overhead reflux loop has a reflux ratio of greater than 4.5:1.

10. The process of claim 9 wherein the third overhead reflux loop has a reflux ratio of greater than 8:1.

11. The process of claim 7 wherein the water extractable impurity in the waste solvent acetonitrile is isopropyl acetate.

12. The process of claim 7 wherein the crude acetonitrile contains acrylonitrile as an impurity.

13. A process for treating crude acetonitrile substantially free of hydrogen cyanide comprising feeding water and the crude acetonitrile into the upper portion of a first distillation column affixed with a first overhead reflux loop at a first pressure of at least 1 atmosphere and distilling the crude acetonitrile in the presence of the water for a time sufficient to allow water extractable impurities to be extractively distilled and removed as an overhead stream from the first distillation column and producing a first acetonitrile-water azeotrope as a side draw from the first distillation column substantially free of impurities and a first bottom product containing water, distilling the first azeotrope in a second distillation column affixed with a second overhead reflux loop at a second pressure less than 1 atmosphere to separate the first azeotrope into a second bottoms product containing water and a second acetonitrile-water azeotrope having a greater concentration of acetonitrile than the first azeotrope, distilling the second azeotrope in a third distillation column affixed with a third overhead reflux loop at a third pressure above 1 atmosphere to produce a third acetonitrile/water azeotrope containing substantially all the water from the second azeotrope, a third bottoms product comprising acetonitrile and heavy organics, and a sidestream comprising purified acetonitrile.

* * * * *